US00PP36707P2

(12) United States Plant Patent
VandenLangenberg

(10) Patent No.: US PP36,707 P2
(45) Date of Patent: May 27, 2025

(54) STRAWBERRY PLANT NAMED 'CBC017'

(50) Latin Name: ***Fragaria* x *ananassa***
Varietal Denomination: CBC017

(71) Applicant: California Berry Cultivars, LLC, French Camp, CA (US)

(72) Inventor: Kyle M VandenLangenberg, Tracy, CA (US)

(73) Assignee: California Berry Cultivars, LLC, French Camp, CA (US)

( * ) Notice: Subject to any disclaimer, the term of this patent is extended or adjusted under 35 U.S.C. 154(b) by 0 days.

(21) Appl. No.: 18/748,611

(22) Filed: Jun. 20, 2024

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./209
CPC ..... A01H 5/08; A01H 5/00; A01H 6/7409; A01H 6/74
See application file for complete search history.

(56) References Cited

U.S. PATENT DOCUMENTS

| | | | | |
|---|---|---|---|---|
| PP19,767 | P2 * | 2/2009 | Shaw | A01H 5/08 Plt./209 |
| PP26,709 | P3 | 5/2016 | Larson et al. | |
| PP27,830 | P3 | 4/2017 | Shaw et al. | |
| 9,919,767 | B2 | 3/2018 | Reid et al. | |

OTHER PUBLICATIONS

CPVO Application Consultation Version 4.21.19, *Fragaria* CBC017, retrieved on Jan. 16, 2025 at https://online.plantvarieties.eu/publicConsultationDetails?registerId=20242322&denomination=cbc017, 2 pp. (Year: 2025).*

* cited by examiner

*Primary Examiner* — June Hwu
(74) *Attorney, Agent, or Firm* — Phase M Legal

(57) ABSTRACT

A new and distinct cultivar of strawberry plant (*Fragaria* x *ananassa*) named 'CBC017' is presented here. This new day-neutral strawberry cultivar is characterized by moderate vigor plants which produce exceptionally large yields of attractive conical to round fruit. In addition, plants of 'CBC017' are resistant to *Fusarium oxysporum f.* sp *fragariae.*

5 Drawing Sheets

Latin name of the genus and species of the plant claimed: Botanical classification: *Fragaria* x *ananassa.*

Variety denomination: The new strawberry variety denomination is 'CBC017'.

BACKGROUND OF THE INVENTION

This invention relates to a new and distinctive day-neutral type cultivar designated as 'CBC017'. The new cultivar was the result of a controlled cross performed in 2017 in Huelva, Spain between the cultivar 'Fronteras' (U.S. Plant Pat. No. 26,709) and the cultivar 'Cabrillo' (U.S. Plant Pat. No. 27830). 'CBC017' was first fruited at an experimental orchard near French Camp, Calif. in 2017, where it was selected, originally designated 117.059-118, and propagated asexually by runners. Following selection and during testing, the plant of this selection was later designated 'CBC017'. Asexual propagules from this original source have been tested in Watsonville, Calif., in Oxnard, Calif., and to a limited extent in grower fields starting in 2022. The cultivar is stable and reproduces true to type in successive generations of asexual reproduction.

COMPARISON WITH PARENTS

'Fronteras' is a short-day cultivar that was selected for its overall high appearance score, large fruit, and high yield. Plants of the parent 'Fronteras' are larger than 'CBC017'.

The parent 'Cabrillo' is a day-neutral cultivar that was selected for its high yield and firm fruit. Plants of 'Cabrillo' are similar in size to 'CBC017'.

SUMMARY OF THE INVENTION

'CBC017' is a day-neutral cultivar that produces fruit over an extended period when treated appropriately in arid, sub-tropical climates. When treated with appropriate planting regimes, 'CBC017' has larger fruit and produces individual plant yields greater than that of either parent. The following traits have been repeatedly observed over multiple testing years and locations and are determined to be unique characteristics of 'CBC017'. These characteristics in combination distinguish 'CBC017' as a new and distinct Strawberry plant:

1. Medium sized plant with open canopy.
2. Day-neutral flowering habit.
3. Large glossy red fruit.
4. Fruit postharvest longevity is good.
5. High yields.

The cultivar 'CBC017', when planted under appropriate conditions, follows a typical day-neutral fruiting pattern, with fruit production occurring regardless of day length and temperature. Fruit quality is good with excellent flavor. Total yield is of increased interest to fresh market strawberry sales companies as increased yields result in increased profits. In addition to its early yield performance, 'CBC017' is resistant to *Fusarium oxysporum f.* sp *fragariae*, the causal agent of *Fusarium wilt.*

BRIEF DESCRIPTION OF THE FIGURES

The accompanying color photographs, identified as FIGS. 1 through 5, show the appearance of typical specimens of the new strawberry cultivar designated 'CBC017'. These Figures depict the colors, as nearly true as it is reasonably possible given differences in color illustrations of this character. Accordingly, color in the photographs may differ slightly from the colors discussed in the botanical description.

DETAILED BOTANICAL DESCRIPTION OF THE PLANT

Figure 1:
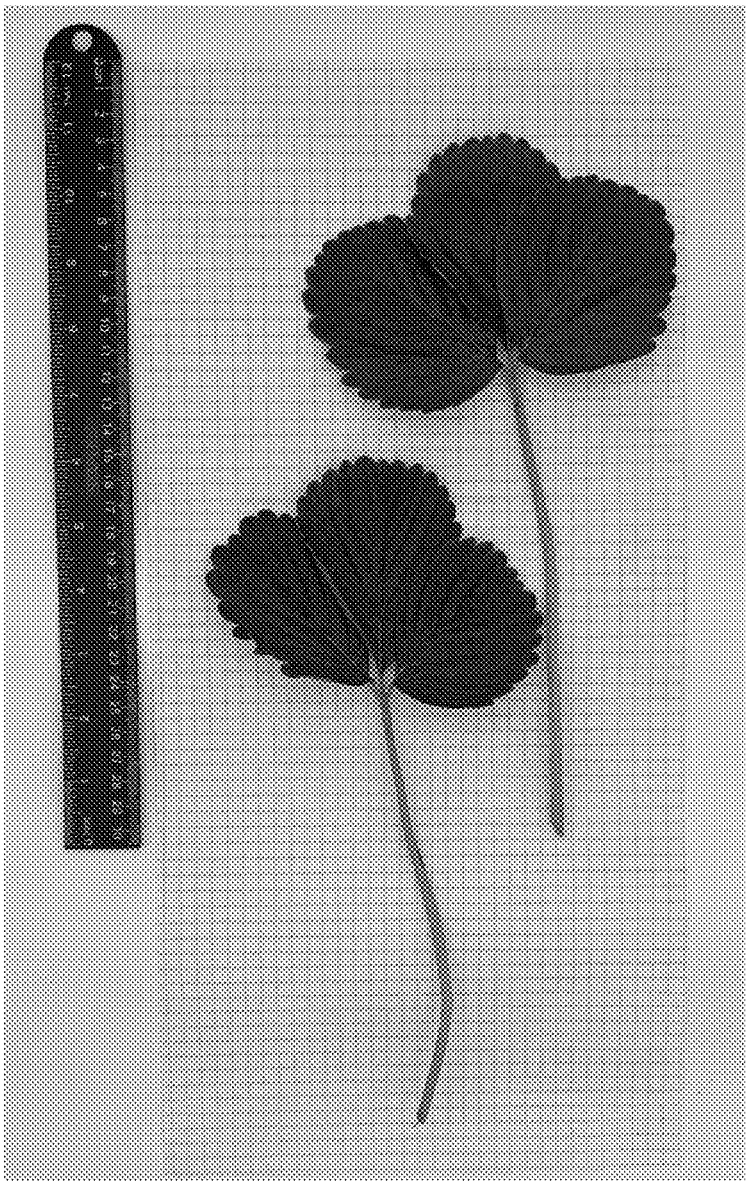
FIG. 1 shows a typical leaf and petiole structure.
Figure 2:
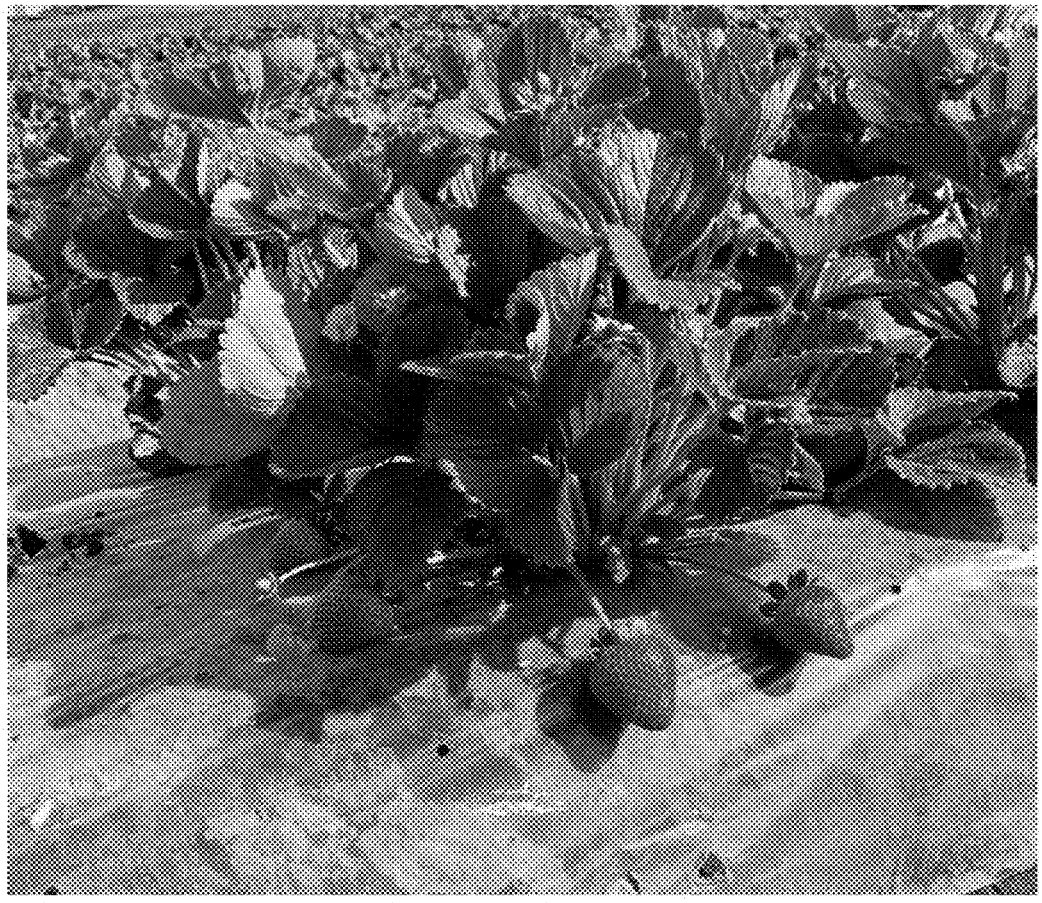
FIG. 2 shows a typical plant and fruit early season.
Figure 3:
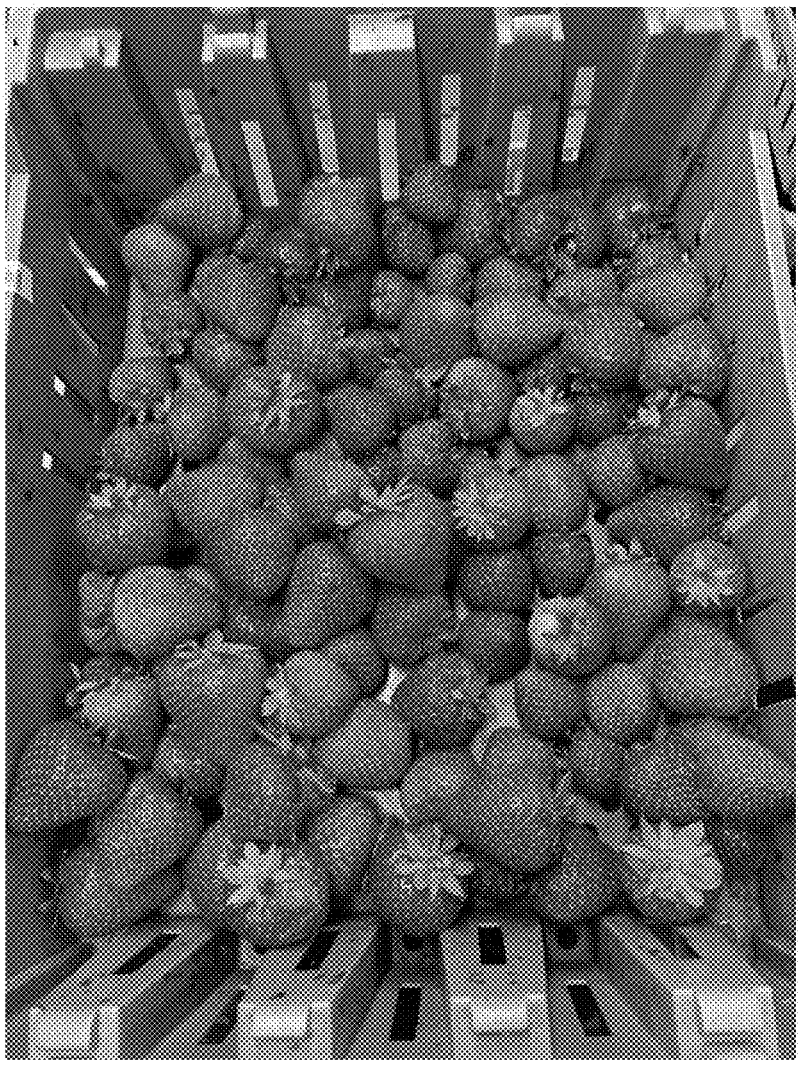
FIG. 3 shows typical fruit in a box.

'CBC017' is a new and distinct day-neutral cultivar of strawberry, genus and species *Fragaria* x *ananassa*. It is the result of a controlled cross between the cultivar 'Fronteras' and the cultivar 'Cabrillo'. Plants of 'CBC017' bloom continuously in higher elevation plantings, and bloom in the heat of low elevation nursery locations such as French Camp, CA, consistent with other day-neutral varieties. The plants of the new cultivar have a moderate vigor and produce multiple crowns during the growing season. 'CBC017' exhibits several characteristics which are improvements over one or both of its parent varieties, and other cultivars known to the Inventor. These characteristics are compared with other cultivars in Table 2, 3, and 4.

The fruit size of 'CBC017' is large, with a seasonal average of 36.4 g, larger than its parents. The fruit size of 'CBC017' is ideal since it is not too large to be damaged in shipping containers, but not too small to allow for efficient picking and packing. The 'CBC017' plant canopy also remains open throughout the season, which makes for greater visibility and ease of picking. Storability of the fruit has not been measured but in informal observations the fruit retains good physical characteristics and appearance for several days after harvest at room temperature and up to at least a week in common refrigerator conditions of roughly 3° C.

'CBC017' produces conic to slightly round fruit like its parent 'Cabrillo', while the fruit of 'Fronteras' is a longer conic shape that often suffers for color problems late in the season. The fruit of 'CBC017' generally ripens evenly from the tip to the shoulders of the berry, resulting in a uniform light red color over the whole fruit. In contrast, the fruit of 'Cabrillo' has darker fruit and can produce fruit with white shoulders early in the season. The fruit of 'CBC017' is firmer than its parent 'Fronteras'.

The data set for 'CBC017' set forth below was collected in May 2023 from plants grown at a test plot in Watsonville, CA. Yield, size, and firmness data is either averaged over the entire 2022-2023 growing season or presented as monthly totals at the same location. As a day-neutral everbearing variety, 'CBC017' begins flowering immediately after planting and continues year-round, producing fruit continuously. Time to the first marketable fruit is roughly five months from planting. Description data was collected on five-month-old plants.

The observed characteristics of 'CBC017' are set forth in Table 1, 2, 3, and 4 below. Color terminology, where noted, is in accordance with the Munsell Colorchart. The observed characteristics of 'CBC017' are also compared to parent cultivars 'Fronteras' and 'Cabrillo' and to 'Monterey' (U.S. Plant Pat. No. 19,767), the closest cultivar known to the Inventor, in Table 2, 3, and 4. Table 5 sets forth the test results of DNA fingerprinting using eight SSR markers.

TABLE 1

Detailed Description of Characteristics of 'CBC017'

| | |
|---|---|
| SPECIFICATION: | |
| Genus/Species | *Fragaria* X *ananassa* |
| Market Name | Strawberry |
| PARENTS: | |
| Female | 'Fronteras' |
| Male | 'Cabrillo' |
| PLANT: | |
| Type | Day-neutral, everbearing |
| Growth Habit | Semi-upright |
| Foliage density | Moderate to light |
| Vigor | Moderate |
| Height | Average 30 cm; range 28-32 cm |
| Width | Average 43 cm; range 35-50 cm |
| Disease tolerance | Test plots have shown tolerance to *Fusarium oxysporum* f. sp *fragariae* |
| LEAF: | |
| Width | Average 11 cm; range 10-12 cm |
| Color | Adaxial surface: 2.5 GY 4/3<br>Abaxial surface: 5 GY 5/6 |
| Adaxial Pubescence | Medium density |
| Adaxial Glossiness | Medium |
| Rugosity | Not present |
| Variegation | Not present |
| TERMINAL LEAFLET | |
| Length | Average 82 mm; range 80-85 |
| Width | Average 81 mm; range 73-86 |
| Ratio (length/width) | 1.0 |
| Margins | Serrate |
| Leaflet shape | Round |
| Base shape | Cuneate |
| Cross-section shape | Concave |
| PETIOLE | |
| Pubescence | Medium density |
| Attitude | Upwards |
| Petiole color | 5 GY 6/8 |
| Petiole length | Average 20 cm; range 14-23 cm |
| Petiole diameter | Average 4.2 mm; range 4.0-4.6 mm |
| STIPULE | |
| Anthocyanin coloration | Light |
| Length | Average 38.5 mm; range 34-42 mm |
| Width | Average 7 mm, range 6.4-8.1 mm |
| INFLORESCENCE: | |
| Flowering | Everbearing |
| Position | Mostly at or above canopy |
| Petal arrangement | Slightly overlapping |
| Petal shape | Actinomorphic and Rotate |
| Calyx size | Larger than corolla |
| Sepal shape | Acute |
| Number of blooms | 8 |
| Length | 3.5 cm |
| Flower diameter | Average 35 mm; range 32-37 mm |

TABLE 1-continued

Figure 4:
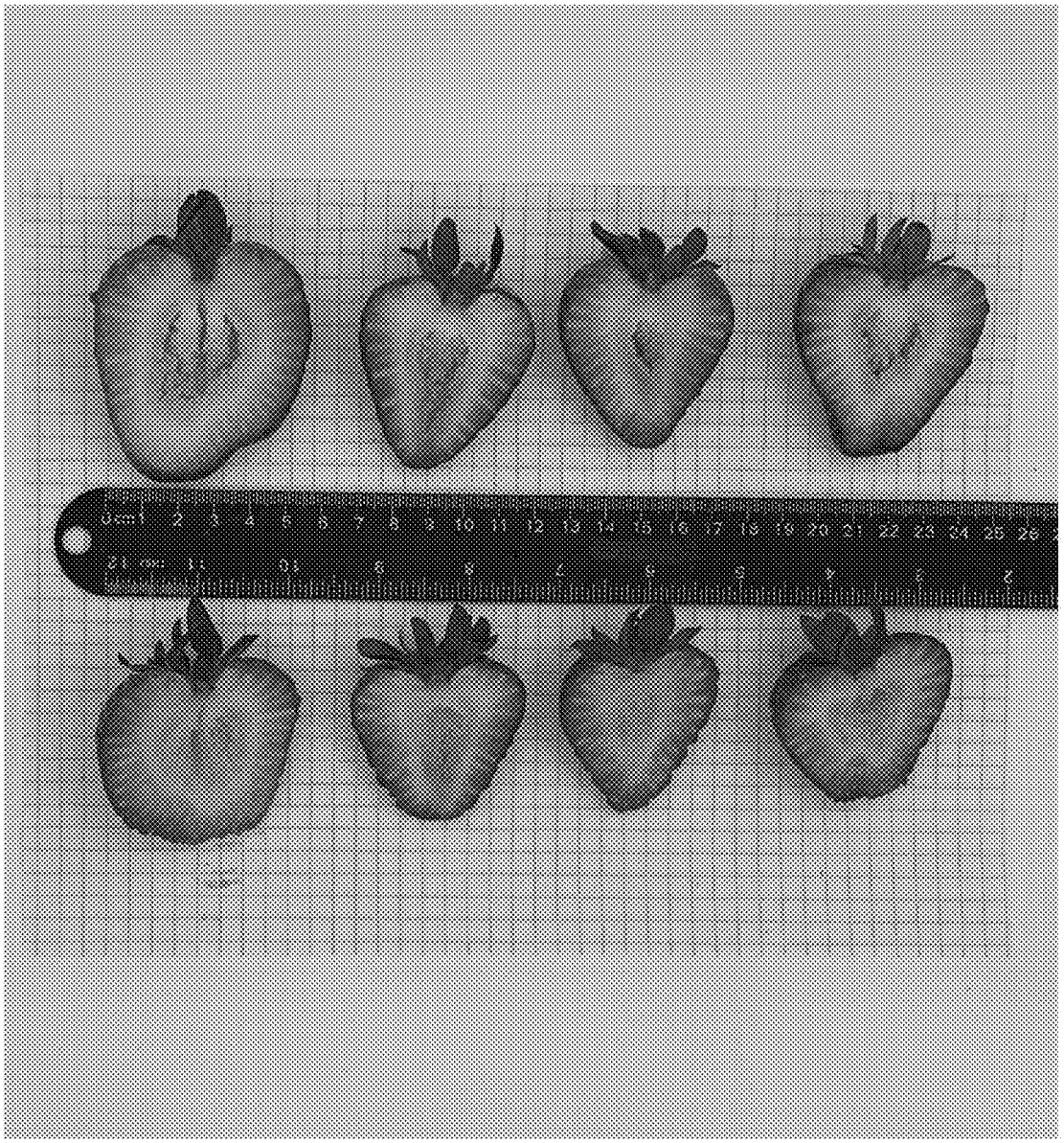
FIG. 4 shows a cross-section of representative fruit mid-season.
Figure 5:
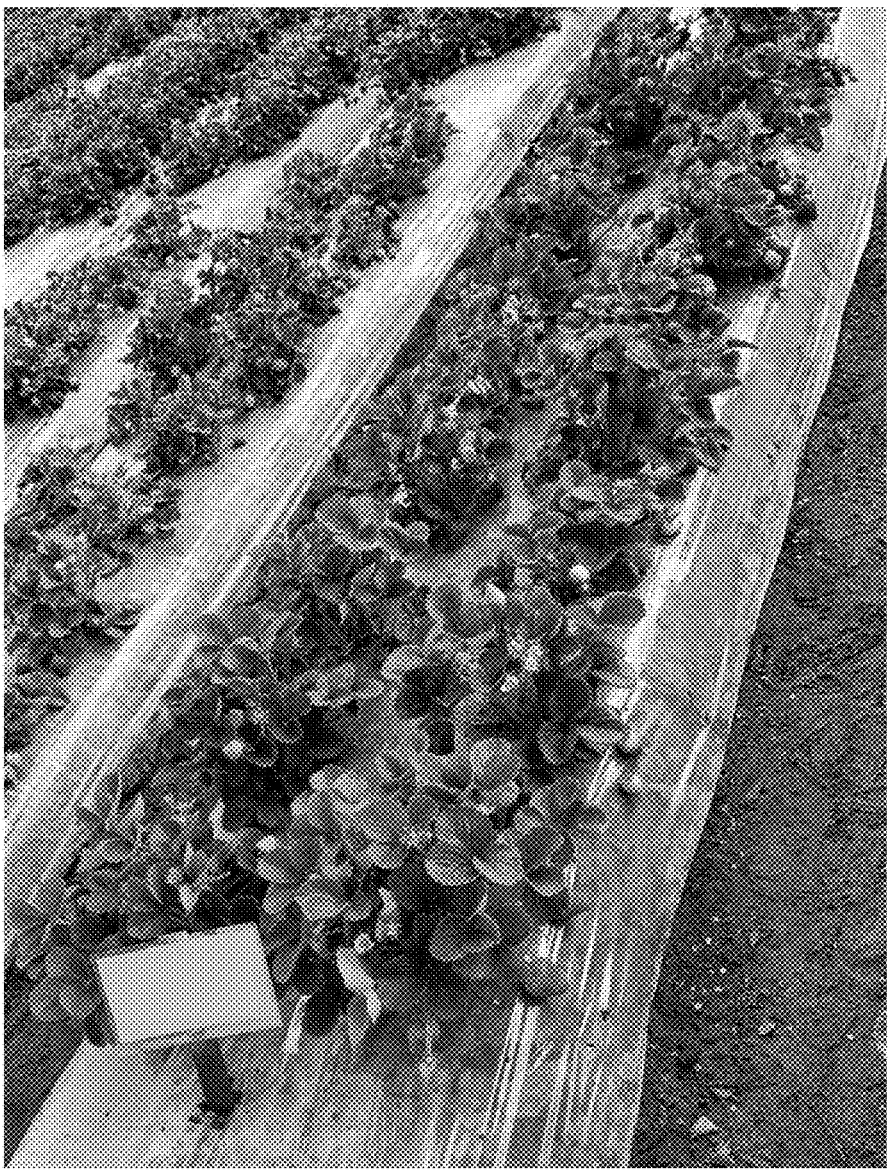
FIG. 5 shows a typical plot in the field of plants and fruit.

| Detailed Description of Characteristics of 'CBC017' | |
|---|---|
| Petal number | Average 5; range 4-6 |
| Petal length | Average 10 mm; range 9-11 mm |
| Petal width | Average 10 mm; range 9-11 mm |
| Ratio (length/width) | 1.0 |
| Calyx color | Adaxial surface: 5 GY 8/8<br>Abaxial surface: 5 GY 6/8 |
| Stamens length | Average 25 mm; range 21-28 mm |
| PEDICEL | |
| Pubescence | Medium density |
| Length | 167 mm |
| Width | 4.1 mm |
| Ratio (length/width) | 41 |
| Color | 2.5 GY 8/9 |
| FRUIT: | |
| Bearing | Day-neutral, everbearing |
| Individual fruit weight | Seasonal average: 37.8 g |
| Shape | Mostly conic, some slightly round |
| Size | Width: 5 cm avg; range 4 to 6 cm (See FIG. 4)<br>Length: 8 cm avg; range 7.5 to 9 cm (see FIG. 4) |
| Achenes | Just below fruit surface |
| Glossiness | Medium/high |
| External color evenness | Even |
| External color | 7.5 R 4/11 |
| Internal color | 7.5 R 5/13 |
| Band at top without achenes | Narrow width |
| Fruit Yield | Grams per plant: 2922 g |
| Firmness | 0.48 kg/force |
| Achene color | 7.5 R 4/11 |
| Achene density | Medium |
| Fruit center hollowness | Small |
| Calyx attachment | Level with fruit |
| Calyx adherence | Adheres when fully ripe |
| Calyx size to fruit | Smaller than fruit |

TABLE 2

Marketable yield of 'CBC017' compared to the cultivars known to the Inventor in Watsonville, CA during the 2022-2023 season.

| | Marketable yield (g/plant) | | | | | |
|---|---|---|---|---|---|---|
| Cultivar | April | May | June | July | August | Total |
| 'Fronteras' | 390 | 624 | 901 | 309 | 87 | 2311 |
| 'Cabrillo' | 205 | 464 | 1039 | 473 | 197 | 2378 |

TABLE 2-continued

Marketable yield of 'CBC017' compared to the cultivars known to the Inventor in Watsonville, CA during the 2022-2023 season.

| | Marketable yield (g/plant) | | | | | |
|---|---|---|---|---|---|---|
| Cultivar | April | May | June | July | August | Total |
| 'Monterey' | 290 | 522 | 957 | 399 | 205 | 2373 |
| 'CBC017' | 305 | 621 | 1236 | 503 | 256 | 2922 |

TABLE 3

Size of 'CBC017' compared to the cultivars known to the Inventor in Watsonville, CA during the 2022-2023 season.

| | Fruit size (g/fruit) | | | | | |
|---|---|---|---|---|---|---|
| Cultivar | April | May | June | July | August | Average |
| 'Fronteras' | 43.4 | 40.8 | 31.0 | 23.7 | 23.9 | 32.6 |
| 'Cabrillo' | 38.2 | 43.9 | 35.0 | 27.1 | 24.9 | 33.8 |
| 'Monterey' | 37.5 | 40.1 | 33.7 | 25.4 | 23.2 | 32.0 |
| 'CBC017' | 48.1 | 49.9 | 38.1 | 28.1 | 25.0 | 37.8 |

| | Firmness (kg/force) | | | |
|---|---|---|---|---|
| Cultivar | May | June | July | Average |
| 'Fronteras' | 0.49 | 0.39 | 0.37 | 0.41 |
| 'Cabrillo' | 0.59 | 0.49 | 0.48 | 0.52 |
| 'Monterey' | 0.55 | 0.51 | 0.46 | 0.51 |
| 'CBC017' | 0.54 | 0.45 | 0.45 | 0.48 |

TABLE 5

DNA finger printing results of eight SSR markers.

| | Allelic Fingerprint Analysis | | | | | | | |
|---|---|---|---|---|---|---|---|---|
| Cultivar | M1 | M2 | M3 | M4 | M5 | M6 | M7 | M8 |
| 'CBC017' | 204, 212, 224 | 259, 264, 269, 271, 275 | 188, 232 | 279, 281, 289 | 156 | 238, 242, 257, 262 | 121, 214, 130, 139 | 213, 215, 228 |

I claim:

1. A new and distinct strawberry plant named 'CBC017' as described and illustrated herein.

* * * * *